US00PP21818P2

(12) United States Plant Patent
de Groot

(10) Patent No.: US PP21,818 P2
(45) Date of Patent: Mar. 29, 2011

(54) ***FICUS* PLANT NAMED 'GREEN KINKY'**
(50) Latin Name: *Ficus benjamina*
Varietal Denomination: Green Kinky

(75) Inventor: Leonardus S. J. de Groot, Langeweg (NL)

(73) Assignee: Kwekerij J. de Groot B.V., Langeweg (NL)

( * ) Notice: Subject to any disclaimer, the term of this patent is extended or adjusted under 35 U.S.C. 154(b) by 0 days.

(21) Appl. No.: 12/655,764

(22) Filed: Jan. 6, 2010

(51) Int. Cl.
*A01H 5/00* (2006.01)

(52) U.S. Cl. ..... Plt./211
(58) Field of Classification Search ..... Plt./211

See application file for complete search history.

*Primary Examiner*—Annette H Para
(74) *Attorney, Agent, or Firm*—C. A. Whealy

(57) ABSTRACT

A new and distinct cultivar of *Ficus* plant named 'Green Kinky', characterized by its compact, upright and outwardly spreading plant habit; freely branching habit; durable dark green-colored leaves that resist abscission; and good postproduction longevity.

2 Drawing Sheets

Botanical designation: *Ficus benjamina.*
Cultivar denomination: 'GREEN KINKY'.

BACKGROUND OF THE INVENTION

The present Invention relates to a new and distinct cultivar of *Ficus* plant, botanically known as *Ficus benjamina*, and hereinafter referred to by the name 'Green Kinky'.

The new *Ficus* plant originated as a naturally-occurring branch mutation of *Ficus benjamina* 'Kinky', not patented. The new *Ficus* plant was discovered and selected by the Inventor on a single plant within a population of plants of 'Kinky' in a controlled greenhouse environment in Langeweg, The Netherlands in February, 2008.

Asexual reproduction of the new *Ficus* plant by cuttings taken in a controlled greenhouse environment in Langeweg, The Netherlands since February, 2008, has shown that the unique features of this new *Ficus* plant are stable and reproduced true to type in successive generations.

SUMMARY OF THE INVENTION

Plants of the new *Ficus* have not been observed under all possible environmental conditions. The phenotype may vary somewhat with variations in environment such as temperature and light intensity without, however, any variance in genotype. The following traits have been repeatedly observed and are determined to be the unique characteristics of 'Green Kinky'. These characteristics in combination distinguish 'Green Kinky' as a new and distinct cultivar of *Ficus:*

1. Compact, upright and outwardly spreading plant habit.
2. Freely branching habit.
3. Durable dark green-colored leaves that resist abscission.
4. Good postproduction longevity.

Plants of the new *Ficus* differ from plants of the parent, 'Kinky', primarily in leaf color as plants of 'Kinky' have green and white variegated leaves.

Plants of the new *Ficus* can be compared to the plants of *Ficus benjamina* 'Natasja', not patented. In side-by-side comparisons conducted in Langeweg, The Netherlands, plants of the new *Ficus* differed from plants of the 'Natasja' in the following characteristics:

1. Plants of the new *Ficus* were more compact than plants of 'Natasja'.
2. Leaves of plants of the new *Ficus* resisted abscission whereas leaves of plants of 'Natasja' were susceptible to abscission.

BRIEF DESCRIPTION OF THE PHOTOGRAPHS

The accompanying colored photographs illustrate the overall appearance of the new *Ficus* plant. These photographs show the colors as true as it is reasonably possible to obtain in colored reproductions of this type. Colors in the photographs may differ slightly from the color values cited in the detailed botanical description, which accurately describe the colors of the new *Ficus* plant.

The photograph on the first sheet comprises a side perspective view of a typical plant of 'Green Kinky' grown in a container.

The photograph on the second sheet is a close-up view of a typical leaves and stems of 'Green Kinky'.

DETAILED BOTANICAL DESCRIPTION

The aforementioned photographs and following observations and measurements describe plants grown in 12-cm containers in Langeweg, The Netherlands in a glass-covered greenhouse during the autumn and early winter under commercial production conditions. During the production of the plants, day temperatures ranged from 18° C. to 25° C., night temperatures ranged from 18° C. to 22° C. and light levels ranged from 550 to 650 Watts $m^2$. Plants were six months old when the photographs and description were taken. In the following description, color references are made to The Royal Horticultural Society Colour Chart, 2007, except where general terms of ordinary dictionary significance are used.

Botanical classification: *Ficus benjamina* 'Green Kinky'.

Parentage: Naturally-occurring branch mutation of *Ficus benjamina* 'Kinky', not patented.

Propagation:

*Type.*—By cuttings.

*Time to initiate roots, summer.*—About 20 days at temperatures of 24° C.

*Time to initiate roots, winter.*—About 27 days at temperatures of 24° C.

*Time to produce a rooted young plant, summer.*—About 30 days at temperatures of 21° C.

*Time to produce a rooted young plant, winter.*—About 37 days at temperatures of 21° C.

*Root description.*—Fine, fibrous; light brown in color.

*Rooting habit.*—Freely branching; moderately dense.

Plant description:

*Plant form and growth habit.*—Compact, upright and outwardly spreading plant habit; roughly globular in shape; low vigor; moderate growth rate.

*Branching habit.*—Freely branching habit; about 22 primary lateral branches develop per plant each with numerous secondary laterals.

*Postproduction longevity.*—Plants of the new *Ficus* have exhibited good postproduction longevity as leaves are durable and resist abscission.

*Plant height.*—About 21.9 cm.

*Plant diameter, area of spread.*—About 32 cm.

*Lateral branch description.*—Length: About 10.8 cm. Diameter: About 2.5 mm. Internode length: About 1.4 cm. Strength: Moderately strong, flexible. Texture: Smooth, glabrous. Color, young stems: Close to 146B to 146C. Color, older stems: Close to 148A.

*Foliage description.*—Arrangement: Alternate, simple. Length: About 5 cm. Width: About 1.8 cm. Shape: Ovate. Apex: Narrowly apiculate to aristate. Base: Attenuate. Margin: Entire, undulate. Venation pattern: Pinnate. Texture, upper and lower surfaces: Smooth, glabrous; leathery. Color: Developing leaves, upper surface: Close to 143B to 143C. Developing leaves, lower surface: Between 143C and 144B. Fully expanded leaves, upper surface: Darker than between 139A and 147A; venation, close to 143A. Fully expanded leaves, lower surface: Between 137D and 47B; venation, close to 144B to 144C.

*Petiole.*—Length: About 1 cm. Diameter: About 1 mm. Texture, upper and lower surfaces: Smooth, glabrous. Color, upper and lower surfaces: Close to 144B.

*Stipules.*—Quantity/arrangement: Two, with one on each side of the petiole. Length: About 1 cm. Width: About 0.75 mm. Shape: Filiform. Color: Close to N144A, color becoming closer to 199A to 199B with development.

Flower description: Flower initiation and development have not been observed on plants of the new *Ficus*.

Temperature tolerance: Plants of the new *Ficus* have been observed to tolerate high temperatures of about 40° C. and to be hardy to USDA Hardiness Zone 10.

Disease/pest tolerance: Plants of the new *Ficus* have not been observed to be resistant to pathogens and pests common to *Ficus*.

It is claimed:

1. A new and distinct cultivar of *Ficus* plant named 'Green Kinky' as illustrated and described.

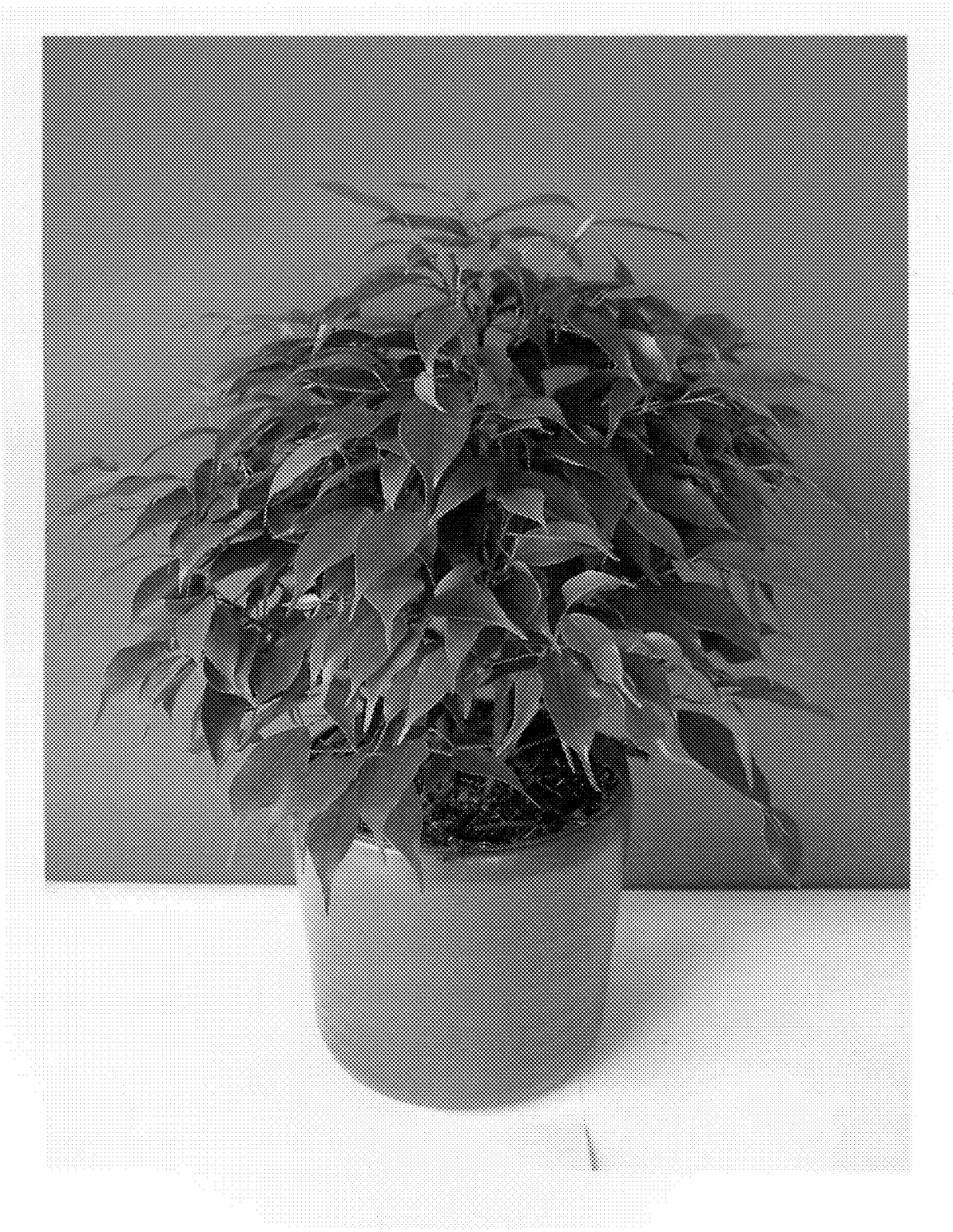

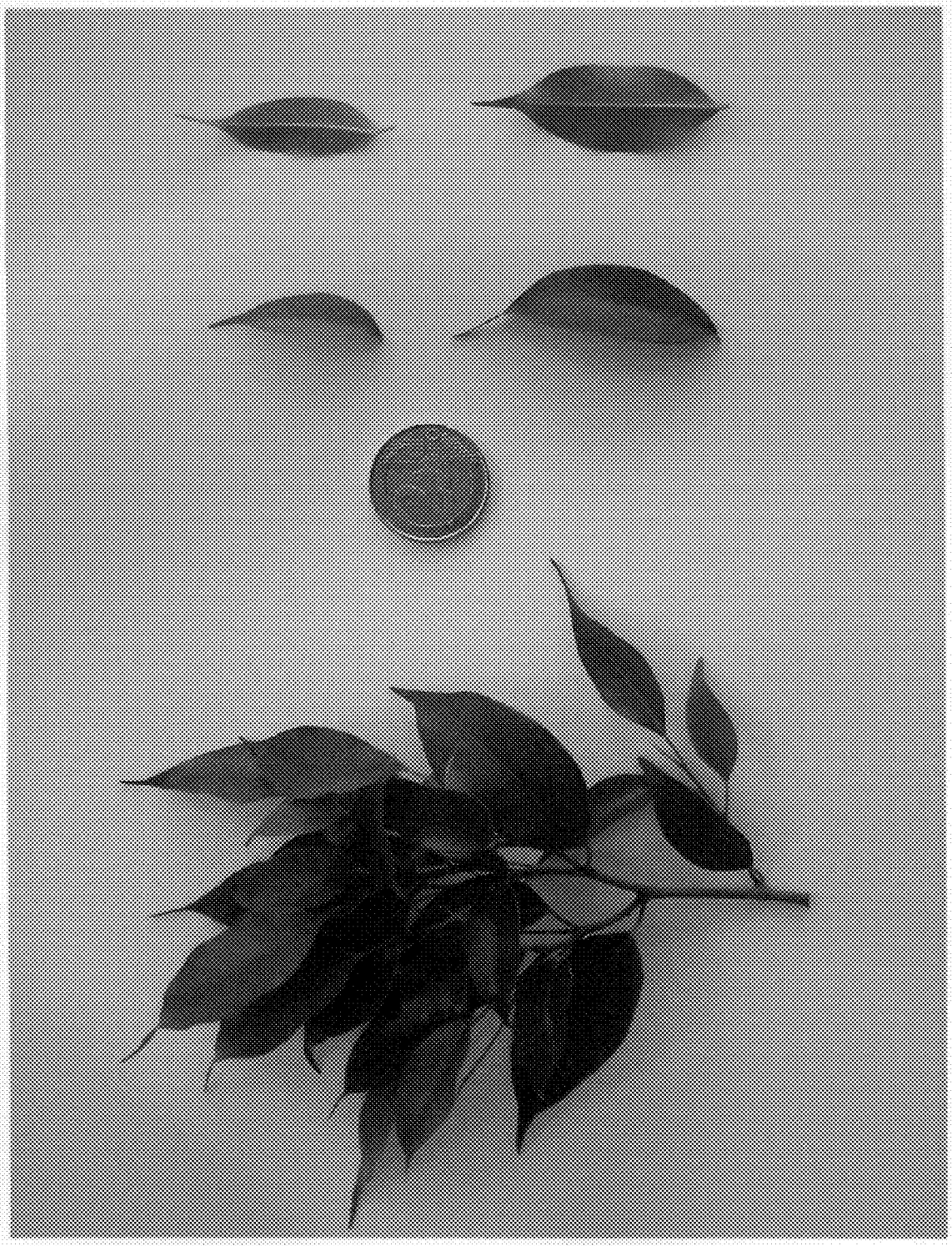

* * * * *